United States Patent
Wang et al.

(10) Patent No.: US 8,366,641 B2
(45) Date of Patent: Feb. 5, 2013

(54) POSTURE DETECTOR CALIBRATION AND USE

(75) Inventors: Hua Wang, Pasadena, CA (US); John Hatlestad, Maplewood, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1354 days.

(21) Appl. No.: 11/283,490

(22) Filed: Nov. 18, 2005

(65) Prior Publication Data

US 2007/0118056 A1    May 24, 2007

(51) Int. Cl.
*A61B 5/103* (2006.01)
*A61B 5/117* (2006.01)

(52) U.S. Cl. ........................... 600/595; 600/587

(58) Field of Classification Search ............ 600/587, 600/595, 300
See application file for complete search history.

(56) References Cited

U.S. PATENT DOCUMENTS

| | | | |
|---|---|---|---|
| 5,593,431 A | | 1/1997 | Sheldon |
| 6,044,297 A | | 3/2000 | Sheldon et al. |
| 6,152,890 A | * | 11/2000 | Kupfer et al. ........... 600/595 |
| 6,625,493 B2 | | 9/2003 | Kroll et al. |
| 7,149,584 B1 | * | 12/2006 | Koh et al. ........... 607/60 |
| 7,471,290 B2 | * | 12/2008 | Wang et al. ........... 345/419 |

FOREIGN PATENT DOCUMENTS

JP    2002200059    7/2002

OTHER PUBLICATIONS

Hansson et al, Validity and Reliability of Triaxial Accelerometers for Inclinometry in Posture Analysis, May 14, 2001, Medical and Biological Engineering and Computing 2001, vol. 39, p. 405-413.*

Brown, An Accelerometer Based Fall Detector: Development, Experimentation, and Analysis, XP-002467922, University of California, Berkeley, Jul. 2005, pp. 1-9.

Bonnet et al., Evaluation of Postural Stability by Means of a Single Inertial Sensor, XP-002467979, Proceedings of the 26th Annual International Conference of the IEEE EMBS, San Francisco, CA, Sep. 1-5, 2004, pp. 2275-2278.

Moe-Nilssen, A new method for evaluating motor control in gait under real-life environmental conditions. Part 1: The instrument, Division of Physiotherapy Science, Faculty of Medicine, University of Bergen, Ulriksdal 8c, N-5009 Bergen, Norway, accepted Nov. 4, 1997, Clinical Biomechanics 13, 1998, pp. 320-327.

Office Action dated Oct. 11, 2010 for European patent application No. 06837769.6, 4 pages.

Office Action Response dated Mar. 11, 2011 for European patent application No. 06837769.6, 8 pages.

Office Action dated Jan. 31, 2012 for European patent application No. 06837769.6, 4 pages.

(Continued)

*Primary Examiner* — Jeffrey G Hoekstra
*Assistant Examiner* — Huong Q. Nguyen
(74) *Attorney, Agent, or Firm* — Schwegman Lundberg & Woessner, P.A.

(57) ABSTRACT

Calibrating a posture detector for a patient's body involves measuring outputs of one or more sensors disposed in relation to the patient's body while the patient assumes a plurality of positions. A transfer matrix is formed having coefficients corresponding to the measured outputs. The transfer matrix defines a relationship between a coordinate system of the one or more sensors and a coordinate system of the patient's body. The body coordinate system is used as a reference coordinate system for posture detection. Posture, including tilt and/or tilt angle, may be determined based on first and second rotational angles defined in relation to the body coordinate system.

42 Claims, 10 Drawing Sheets

OTHER PUBLICATIONS

Office Action Response dated May 24, 2012 for European patent application No. 06837769.6, 9 pages.

Office Action with translation dated Nov. 8, 2011 from Japanese Application No. 2008-541341, 8 pages.

Office Action Response dated Feb. 13, 2012 for Japanese Application No. 2008-541341, 12 pages.

Office Action with translation dated Jul. 30, 2012 from Japanese Application No. 2008-541341, 4 pages.

\* cited by examiner

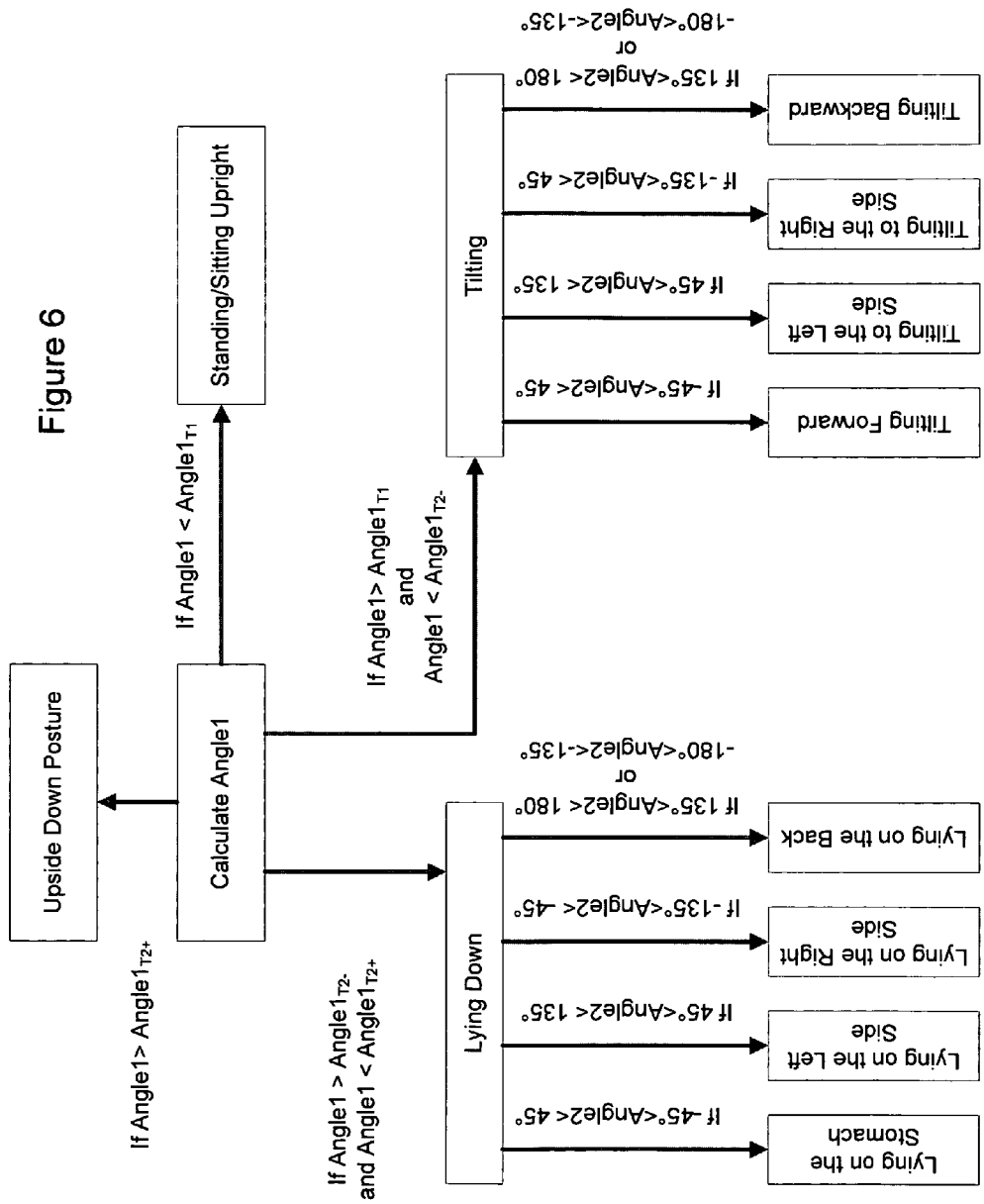

POSTURE DETECTOR CALIBRATION AND USE

FIELD OF THE INVENTION

The present invention relates generally to posture sensing methods and systems.

BACKGROUND OF THE INVENTION

The position or posture of a patient is a factor in various diseases and disorders, including those of the cardiac and/or respiratory systems. Certain disease processes may be exacerbated when the patient assumes particular postures. For example, obstructive sleep apnea episodes may begin or increase in frequency or severity when the patient lies down. In another example, congestive heart failure (CHF) patients frequently sleep with their torso tilted upward to reduce pulmonary congestion. Patient posture information may be used to enhance diagnosis of these and other diseases and disorders.

Posture sensing may also be used to enhance therapy delivery, such as cardiac pacing therapy. For example, changes in body posture can cause sudden decrease in blood pressure. For some patients, particularly the elderly and/or people taking certain medications, inadequate neural control of blood pressure may result in syncope upon rising from a sitting position or other sudden posture changes. Posture sensing may be used to improve cardiac pacing therapy during and after posture changes to promote physiologic pacing.

The present invention describes posture detection methods and systems including processes for calibrating and using posture detectors and offers various advantages over the prior art.

SUMMARY OF THE INVENTION

Embodiments of the invention relate to detection of patient posture. One embodiment of the invention involves a method for sensing posture. The outputs of one or more sensors disposed in relation to a patient's body are measured while the patient assumes a plurality of body postures. The one or more sensors are responsive to a gravitational field. A transfer matrix is formed having coefficients corresponding to the measured outputs. The transfer matrix defines a relationship between a coordinate system of the one or more sensors and a coordinate system of the patient's body. The posture of the patient's body is determined using the body coordinate system as a reference coordinate system. For example, the coefficients of the transfer matrix comprise the measured outputs divided by a magnitude of the gravitational field. At least one of measuring the outputs of the one or more sensors, forming the transfer matrix, and determining the posture of the patient's body may be performed at least in part implantably.

In some implementations, the sensors responsive to the gravitational field are implemented as accelerometers and measuring the outputs of the one or more sensors comprises measuring the outputs of one or more accelerometers. For example, the sensitive angles of at least two the accelerometers may be oriented substantially orthogonally.

In some implementations, the outputs of the one or more sensors are measured while the patient assumes two or more substantially mutually orthogonal body postures. According to one scenario, the outputs of the one or more sensors are measured while the patient is upright or upside down, while the patient is lying on a right side or lying on a left side, and while the patient is prone or supine.

According to one aspect, determining the posture of the patient's body comprises determining tilt or tilt angle of the patient's body. For example, the tilt angle may be determined to within about five to about ten degrees with respect to a plane.

In one implementation, the posture of the patient's body is determined using first and second rotational angles. The first and second rotational angles are determined and are compared to threshold values. Posture of the patient is determined based on the comparison.

Another embodiment of the invention involves a posture detector. The posture detector includes one or more sensors responsive to a gravitational field. Each sensor is disposed in relation to a patient's body and configured to output a signal based on an orientation of the patient. The posture detector further comprises calibration circuitry coupled to the one or more sensors and configured to form a transfer matrix having coefficients corresponding to the sensor outputs. The transfer matrix defines a relationship between a coordinate system of the one or more sensors and a coordinate system of the patient's body. A posture processor is coupled to the one or more sensors and the calibration circuitry. The posture processor is configured to determine a posture of the patient's body using the body coordinate system as a reference coordinate system. The posture processor may be configured to determine a tilt or tilt angle of the patient's body.

For example, the coefficients of the transfer matrix comprise the sensor outputs divided by a magnitude of the gravitational field. At least one of the one or more sensors, the calibration circuitry, and the posture processor may comprise an implantable component.

In one implementation, the sensors comprise accelerometers and the sensitive axes of the accelerometers are oriented substantially orthogonally.

The posture detector may include a diagnostics processor configured to determine a presence cardiac decompensation based on the tilt angle. The diagnostics processor may track progression of disease based on changes in the tilt angle.

Another embodiment of the invention is directed to a posture sensing method. First and first and second rotational angles associated with posture are determined. The first and second rotational angles are compared to threshold values. The posture is based on the comparison of the first and second rotational angles to the threshold values.

According to one aspect of the invention, the first rotational angle comprises a polar angle with respect to a first axis of a body coordinate system the second rotational angle comprises an azimuthal angle within a plane of the second and third axes of the body coordinate system. For example, the first axis of the body coordinate system may be oriented substantially along the inferior-superior axis of the patient's body. The first, second and third axes may be substantially mutually orthogonal, and one of the second or third axes may be oriented substantially along the anterior-posterior axis of the patient's body.

According to one implementation, determining the first and the second rotational angles comprises defining a vector associated with the posture and determining the posture based on an orientation of the vector with respect to a body coordinate system.

The posture sensing method may include determining tilt and/or tilt angle of the patient's body.

A further embodiment of the invention is directed to a posture detector. The posture detector includes one or more sensors responsive to a gravitational field disposed in relation to a patient's body. Each sensor outputs a signal based on an orientation of the patient. The posture detector also includes a posture processor coupled to the one or more sensors. The posture processor is configured to determine first and second rotational angles associated with the posture from the sensor outputs and to determine the posture based on the first and second rotational angles. For example, the one or more sensors may comprise one or more accelerometers.

According to various aspects of the invention, the posture processor is configured to compare the first and the second rotational angles to threshold values and to determine the posture based on the comparisons. The first rotational angle may include a polar angle with respect to a first axis of a body coordinate system. the second rotational angle may include an azimuthal angle within a plane of the second and third axes of the body coordinate system.

In some implementations, the first axis of the body coordinate system may be oriented substantially along the inferior-superior axis of the patient's body. In some implementations, the first, second and third axes are substantially mutually orthogonal, and one of the second or third axes is oriented substantially along the anterior-posterior axis of the patient's body.

The posture processor of the posture detector may be configured to define a vector associated with the posture and to determine the posture, e.g., tilt or tilt angle, based on an orientation of the vector with respect to a body coordinate system.

The above summary of the invention is not intended to describe each embodiment or every implementation of the invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 6 is a flowchart illustrating a posture detection algorithm in accordance with embodiments of the invention;

Figure 1:
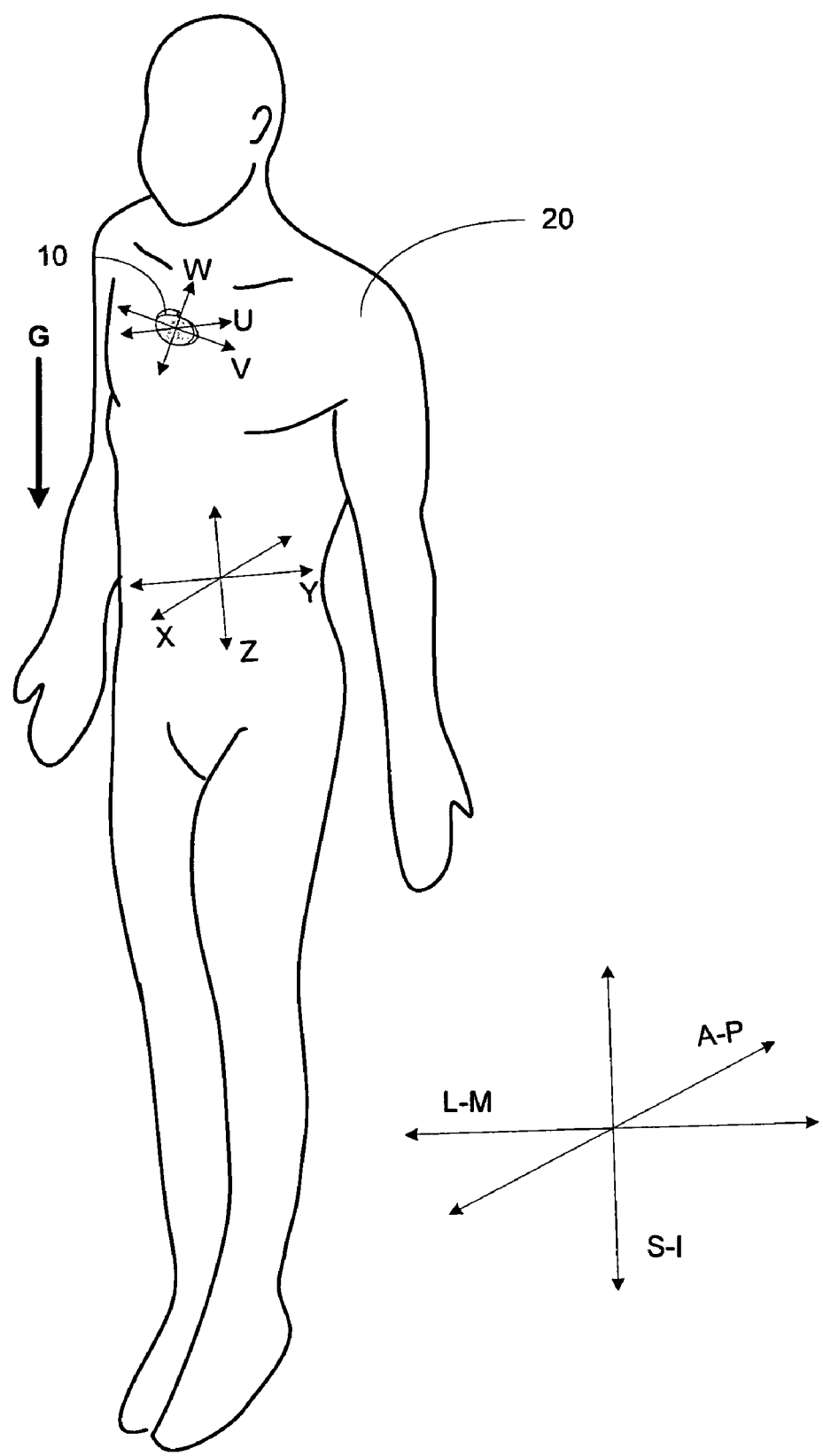
FIG. 1 illustrates a medical device incorporating a posture detector implanted within a patient's body in accordance with embodiment of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which are shown by way of illustration, various embodiments by which the invention may be practiced. It is to be understood that other embodiments may be utilized, and structural and functional changes may be made without departing from the scope of the present invention.

Patient posture is an important factor in the diagnosis of certain medical disorders and may also be used to enhance therapy delivery. Posture detection involves determining an orientation of the patient's body, such as determining if the patient is in a vertical position (upright or upside down), determining if the patient is in a horizontal position (lying on the back, lying on the stomach, lying on the right side or the left side), or determining if the patient's body is tilted to the right, tilted to the left, tilted forward, or tilted backward. Posture detection in accordance with the embodiments described herein may additionally include determining an angle of tilt of the patient's body. Posture information may be tracked over time, stored, and/or correlated to other medical events.

Information about patient posture may be evaluated with respect to the detection of various disorders to determine if an association between patient posture and a particular disorder is present. The posture of the patient's body, such as the inclination of the upper torso, may be linked to various medical disorders, including disorders affecting the respiratory and/or cardiovascular systems. Tracking patient posture over time can be used to assess the general well-being of a patient. For example, if posture information acquired over a period of time indicates that a patient spends an increasing amount of time lying down and/or inactive, the patient's health may be declining. In another example, if the patient's posture indicates a change in sleeping position, such as a shift from sleeping lying down to sleeping sitting up, this change may indicate increased pulmonary congestion related to congestive heart failure (CHF). In yet another example, discriminating between a recumbent and an upright position of the patient's body is useful in determining if a patient is asleep or awake. Diagnosis of various conditions, e.g., sleep apnea, may be enhanced with knowledge of the patient's sleep state. Thus, a patient may be diagnosed as having sleep disordered breathing if breathing interruptions occur while a patient is sleeping, as indicated by patient posture during the disordered breathing episodes.

Knowledge of patient posture may also be used to deliver therapy appropriate to the patient's particular situation. For example, posture information may be used by a cardiac rhythm management (CRM) device with or without information on the activity level of the patient so that cardiac pacing is delivered at a hemodynamically appropriate pacing rate. In another implementation, cardiac pacing may be adjusted if a sudden change in the patient's posture is detected. In yet another implementation, cardiac and/or other types of therapy may be adjusted to accommodate the patient's sleep/wake cycle as determined, at least in part, by the patient posture. For example, a cardiac pacing rate may be decreased from a waking rate to a lower sleeping rate to account for the decreased hemodynamic need of the patient during sleep.

Methods and systems described herein, in accordance with embodiments of the invention, provide for calibration of a multi-axis posture detector comprising one or more sensors responsive to a gravitational field. In further embodiments, methods and systems for determining patient posture based on first and second rotational angles as measured by the multi-axis posture detector are described.

In one implementation, a multi-axis posture detector described herein may be employed in an implanted device to measure three components of the gravitational acceleration vector G in device coordinates. The transformation matrix between the device coordinates, used for measuring the acceleration signals, and the body coordinates, used for determining postures, is acquired during a calibration process. From the acceleration components measured in device coordinates and using the transfer matrix, the patient's postures and activities can be inferred.

FIG. 1 illustrates a medical device 10 incorporating a posture detector implanted within a patient's body 20 in the upper left thoracic region, such as a typical placement for a cardiac pacemaker or defibrillator. The position of the patient's body may be expressed in terms of body coordinates X, Y, and Z. The reference axes for the body coordinate system may be selected to be mutually orthogonal, although non-orthogonal reference axes may alternatively be selected. In one implementation, illustrated in FIG. 1, the X axis of the body coordinate system generally corresponds to the anterior-posterior (A-P) axis of the body, the Y axis generally corresponds to the lateral-medial (L-M) axis of the body, and the Z axis generally corresponds to the superior-inferior (S-I) axis of the body.

The posture detector of the medical device 10 is associated with device coordinate axes U, V, and W. The posture detector may comprise one or more uniaxial orientation sensors, for example, three uniaxial DC accelerometers. Each device coordinate axis, U, V, or W, corresponds to a sensitive axis of one uniaxial accelerometer of the posture detector, which are typically arranged in a mutually orthogonal orientation. As can be observed in FIG. 1, the sensitive axes of the uniaxial accelerometers U, V, and W may not be aligned perfectly with respect to the gravitational acceleration vector G acting on the patient's body 20. In a typical implant implementation, the device axes are tilted slightly or significantly with respect to the vector G. Further, the device axes U, V, and W are not necessarily aligned with body coordinates X, Y, and Z.

The three uniaxial accelerometers may be formed as an integrated device such as a surface micro-machined semiconductor device. In one implementation, each uniaxial accelerometer comprises an inertial mass suspended by compliant springs which are acted on by gravity. The magnitude of the inertial mass deflection is converted to an electrical signal by the surrounding electronics and appears as the sensor output of the uniaxial accelerometer. The output of an accelerometer acted on by the earth's gravitational force provides a characteristic DC output voltage, e.g., maximum output, if the sensitive axis of the accelerometer is aligned with the earth's gravitational field while the accelerometer is at rest. As the patient's body moves, the angle at which the sensitive axis of the accelerometer is tilted with respect to the earth's gravitation force changes and the output of the accelerometer is related to the angle of tilt.

The gravitational vector G is used to designate the direction and magnitude of the force of gravity acting on the patient's body. The position of the patient's body may be expressed in body coordinates by translating the vector gravitational force G acting on the patient's body from device coordinates (U,V,W) to body coordinates (X,Y,Z). Embodiments of the invention involve directly determining the transfer matrix for translating device coordinates (U,V,W) to body coordinates (X,Y,Z).

Figure 2:
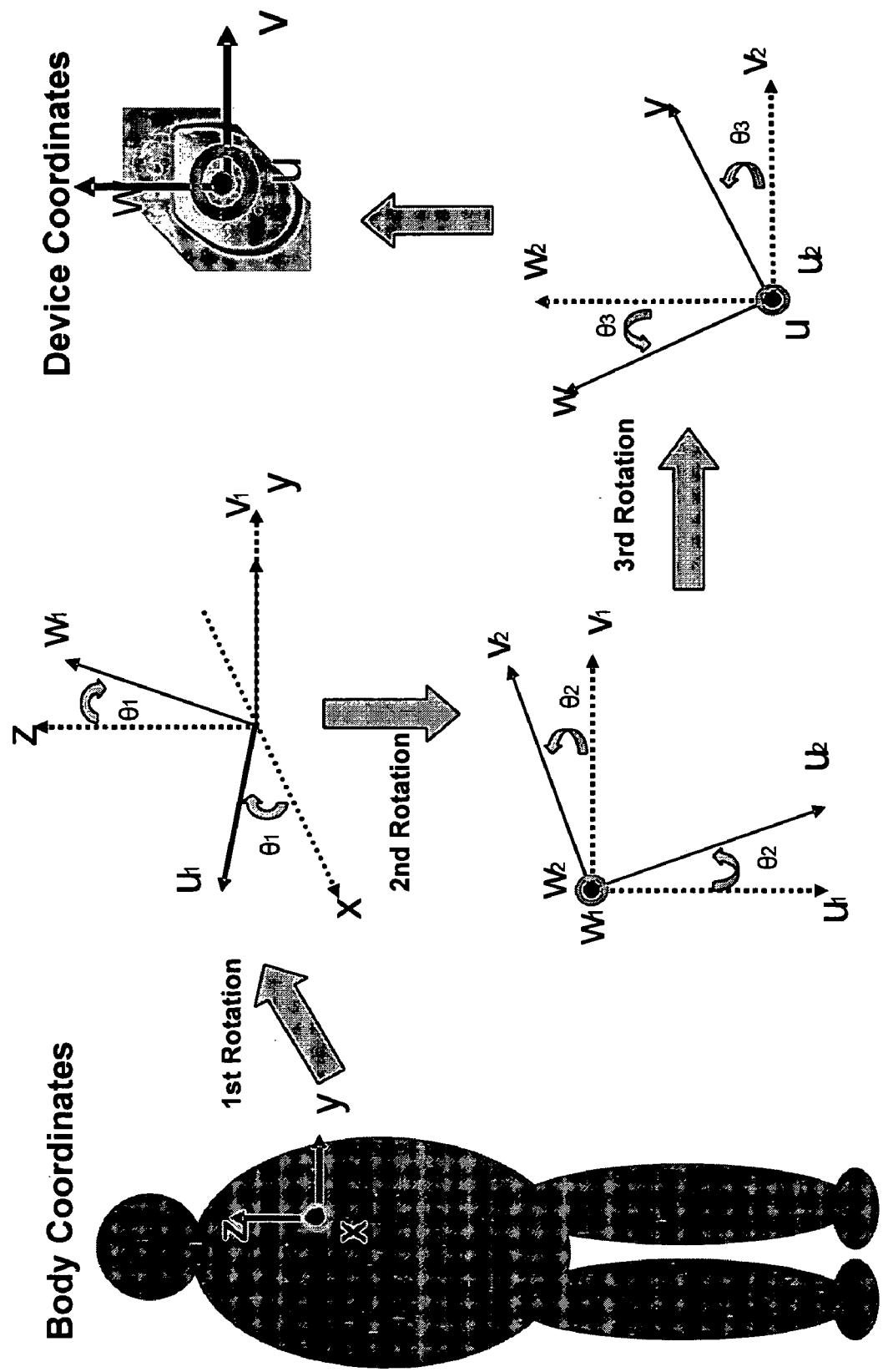
FIG. 2 conceptually illustrates the body coordinate system X,Y,Z and the device coordinate system U,V,W and an approach for converting from body to device coordinates in accordance with embodiments of the invention.

FIG. 2 illustrates the body coordinate system X,Y,Z, the device coordinate system U,V,W and an approach for converting from body to device coordinates in accordance with embodiments of the invention. The transfer matrix used for translating between device coordinates and body coordinates may be derived from the acceleration measurements taken during the three rotations. For the first rotation, $$\begin{bmatrix} a_{u1} \\ a_{v1} \\ a_{w1} \end{bmatrix} = \begin{bmatrix} \cos\theta_1 & 0 & \sin\theta_1 \\ 0 & 1 & 0 \\ -\sin\theta_1 & 0 & \cos\theta_1 \end{bmatrix} \begin{bmatrix} a_x \\ a_y \\ a_z \end{bmatrix} = M_1,$$ Equation 1 where $a_{u1}$ is the force in the U direction during the first rotation, $a_{v1}$ is the force in the V direction during the first rotation, $a_{w1}$ is the force in the W direction during the first rotation, $a_x$ is the force in the X direction during the first rotation, $a_y$ is the force in the Y direction during the first rotation, and $a_z$ is the force in the Z direction during the first rotation.

For the second rotation, $$\begin{bmatrix} a_{u1} \\ a_{v1} \\ a_{w1} \end{bmatrix} = \begin{bmatrix} \cos\theta_2 & \sin\theta_2 & 0 \\ -\sin\theta_2 & \cos\theta_2 & 0 \\ 0 & 0 & 1 \end{bmatrix} \begin{bmatrix} a_{u1} \\ a_{v1} \\ a_{w1} \end{bmatrix} = M_2,$$ Equation 2 where $a_{u2}$ is the force in the U direction during the second rotation, $a_{v2}$ is the force in the V direction during the second rotation, $a_{w2}$ is the force in the W direction during the second rotation.

And for the third rotation, $$\begin{bmatrix} a_{u1} \\ a_{v1} \\ a_{w1} \end{bmatrix} = \begin{bmatrix} 1 & 0 & 0 \\ 0 & \cos\theta_3 & \sin\theta_3 \\ 0 & -\sin\theta_3 & \cos\theta_3 \end{bmatrix} \begin{bmatrix} a_{u1} \\ a_{v1} \\ a_{w1} \end{bmatrix} = M_3,$$ Equation 3 where $a_{u3}$ is the force in the U direction during the second rotation, $a_{v3}$ is the force in the V direction during the second rotation, $a_{w3}$ is the force in the W direction during the second rotation.

The transfer matrix M from body coordinates (X,Y,Z) to device coordinates (U,V,W) may be expressed:

$$\begin{bmatrix} a_u \\ a_v \\ a_w \end{bmatrix} = M_1 M_2 M_3 \begin{bmatrix} a_x \\ a_y \\ a_z \end{bmatrix} = M \begin{bmatrix} a_x \\ a_y \\ a_z \end{bmatrix},$$ Equation 4

Expanding, the transfer matrix may be written as Equation 5:

$$\begin{bmatrix} a_u \\ a_v \\ a_w \end{bmatrix} = \begin{bmatrix} \cos\theta_2\cos\theta_1 & \sin\theta_2 & \cos\theta_2\sin\theta_1 \\ -\cos\theta_3\sin\theta_2\cos\theta_1 - \sin\theta_1\sin\theta_3 & \cos\theta_2\cos\theta_3 & -\cos\theta_3\sin\theta_2\sin\theta_1 + \sin\theta_3\cos\theta_1 \\ \sin\theta_3\sin\theta_2\cos\theta_1 - \cos\theta_3\sin\theta_1 & -\sin\theta_3\cos\theta_2 & \sin\theta_3\sin\theta_2\sin\theta_1 + \cos\theta_1\cos\theta_3 \end{bmatrix} \begin{bmatrix} a_x \\ a_y \\ a_z \end{bmatrix},$$

where, $$\begin{bmatrix} a_u \\ a_v \\ a_w \end{bmatrix}$$

represents the force vector G in device coordinates;

$$\begin{bmatrix} a_x \\ a_y \\ a_z \end{bmatrix} = \text{represents the force vector } G \text{ in body coordinates; and}$$

$$\begin{bmatrix} \cos\theta_2\cos\theta_1 & \sin\theta_2 & \cos\theta_2\sin\theta_1 \\ -\cos\theta_3\sin\theta_2\cos\theta_1 - \sin\theta_1\sin\theta_3 & \cos\theta_2\cos\theta_3 & -\cos\theta_3\sin\theta_2\sin\theta_1 + \sin\theta_3\cos\theta_1 \\ \sin\theta_3\sin\theta_2\cos\theta_1 - \cos\theta_3\sin\theta_1 & -\sin\theta_3\cos\theta_2 & \sin\theta_3\sin\theta_2\sin\theta_1 + \cos\theta_1\cos\theta_3 \end{bmatrix}$$

the transfer matrix M.
Equation 4 may be alternatively written, $$\begin{bmatrix} a_u \\ a_v \\ a_w \end{bmatrix} = M[a_x \quad a_y \quad a_z]^T. \qquad \text{Equation 6}$$

Thus, the transformation between device coordinates (U,V,W) to body coordinates (X,Y,Z) is expressed:

$$[a_x, a_y, a_z]^T = M^{-1}[a_u, a_v, a_w]. \qquad \text{Equation 7}$$

Expanding Equation 7 yields, $$\begin{bmatrix} a_x \\ a_y \\ a_z \end{bmatrix} = M^{-1} \begin{bmatrix} a_u \\ a_v \\ a_w \end{bmatrix} = M_1^{-1} M_2^{-1} M_3^{-1} \begin{bmatrix} a_u \\ a_v \\ a_w \end{bmatrix} \qquad \text{Equation 8}$$

Figure 3:
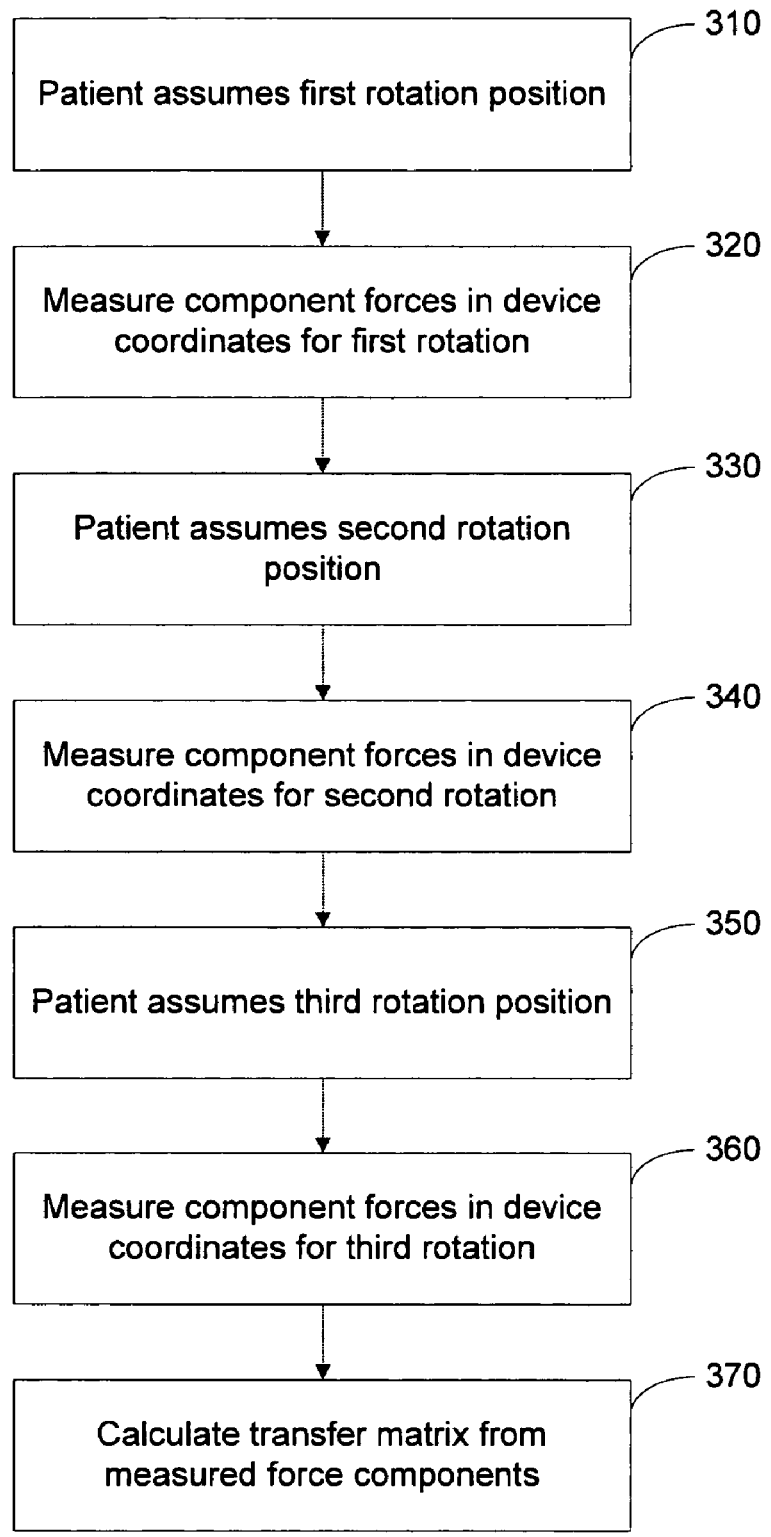
FIG. 3 is a flowchart illustrating a method for determining a calibration transfer matrix for a posture detector in accordance with embodiments of the invention.

A calibration process in accordance with embodiments of the invention involves measuring the components of force in device coordinates (U,V,W) as the patient assumes three positions. The measured force components are used to determine the elements of the transfer matrix. The coefficients of the transfer matrix correspond to the measured force components. Calibration of the transfer matrix in accordance with embodiments of the invention is illustrated in the flowchart of FIG. 3. As illustrated in this example, the matrix coefficients comprise the measured force components divided by the magnitude of the gravitational field, as shown below in equations 12, 14, and 16. The patient assumes 310 a first posture calibration position, e.g., the patient lies on his back. The component forces are measured 320 in device coordinates (U,V,W) for the first rotation. The patient assumes 330 a second posture calibration position, e.g., the patient lies on his right side. The component forces are measured 340 in device coordinates for the second posture calibration position. The patient assumes 350 a third posture calibration position, e.g., the patient stands upright. The component forces are measured 360 in device coordinates for the third posture calibration position. The component forces measured for the first, second, and third posture calibration positions are used to calculate 370 a transfer matrix for relating forces measured in device coordinates (U,V,W) to forces in body coordinates (X,Y,Z).

Direct calibration of the transfer matrix components in accordance with the calibration procedure discussed in connection with FIG. 3 may be algebraically described beginning with Equation 9:

$$\begin{bmatrix} a_u \\ a_v \\ a_w \end{bmatrix} = M \begin{bmatrix} a_x \\ a_y \\ a_z \end{bmatrix} = \begin{bmatrix} M_{11} & M_{12} & M_{13} \\ M_{21} & M_{22} & M_{23} \\ M_{31} & M_{32} & M_{33} \end{bmatrix} \begin{bmatrix} a_x \\ a_y \\ a_z \end{bmatrix}. \qquad \text{Equation 9}$$

Rewriting Equation 9 to express the body coordinates as a function of the device coordinates yields, $$\begin{bmatrix} a_x \\ a_y \\ a_z \end{bmatrix} = M^{-1} \begin{bmatrix} a_u \\ a_v \\ a_w \end{bmatrix}. \qquad \text{Equation 10}$$

The patient lies on his back which aligns the gravity vector along the −x axis of the body coordinate system. During the first posture calibration maneuver, in body coordinates, $$[a_x a_y a_z]^T = [-g\,0\,0]^T. \qquad \text{Equation 11}$$

where g corresponds to the magnitude of the force of gravity. The three components of force are measured in device coordinates are recorded as $a_{ur1}$, $a_{vr1}$, and $a_{wr1}$. Thus, considering Equation 9, the first column of the matrix M can be written as:

$$M_{11} = -\frac{a_{ur1}}{g},\ M_{21} = -\frac{a_{vr1}}{g},\ \text{and}\ M_{31} = -\frac{a_{wr1}}{g}, \qquad \text{Equation 12}$$

where $a_{ur1}$, $a_{vr1}$, and $a_{wr1}$, are the measured forces in the U, V, and W directions, respectively measured during the first rotation.

During the second calibration maneuver, the patient lies on his right side, aligning the gravity vector along the −y axis of the body coordinate system. In body coordinates, $$[a_x, a_y, a_z]^T = [0 \; -g \; 0]^T. \quad \text{Equation 13}$$

The three components of force are measured in device coordinates and recorded as $a_{ur2}$, $a_{vr2}$, and $a_{wr2}$. The second column of the matrix M can be written as:

$$M_{12} = -\frac{a_{ur2}}{g}, \; M_{22} = -\frac{a_{vr2}}{g}, \; \text{and} \; M_{32} = -\frac{a_{wr2}}{g}, \quad \text{Equation 14}$$

where $a_{ur2}$, $a_{vr2}$, and $a_{wr2}$, are the measured forces in the U, V, and W directions, respectively, measured during the second calibration maneuver.

During the third calibration maneuver, the patient stands upright, aligning the gravity vector along the −z axis of the body coordinate system. In body coordinates, $$[a_x, a_y, a_z]^T = [0 \; 0 \; -g]^T. \quad \text{Equation 15}$$

The three components of force are measured in device coordinates are recorded as $a_{ur3}$, $a_{vr3}$, and $a_{wr3}$. The third column of the matrix M can be written as:

$$M_{13} = -\frac{a_{ur3}}{g}, \; M_{23} = -\frac{a_{vr3}}{g}, \; \text{and} \; M_{33} = -\frac{a_{wr3}}{g}, \quad \text{Equation 16}$$

where $a_{ur2}$, $a_{vr2}$, and $a_{wr2}$, are the measured gravitational accelerations in the U, V, and W directions, respectively, measured during the third rotation.

Calibration methods in accordance with embodiments of the invention allow for direct calibration of each element in the transfer matrix, thus reducing calculation errors for the three rotation angles, $\theta_1$, $\theta_2$, and $\theta_3$, and improving the accuracy and reliability of posture system calibration and/or posture detection. Further, if the three rotational postures are substantially mutually orthogonal, then the transfer matrix is invertible even if there exist considerable measurement errors, thus enhancing the reliability of the calibration.

Posture determination in accordance with embodiments of the invention described herein can be implemented using calibration based on "standard" postures which are typically highly orthogonal. However, the patient may rarely perform such highly orthogonal postures in their daily life. Thus, calibrating the posture detection system with the patient's natural postures, although possibly non-orthogonal, may be more informative than orthogonal calibration. Non-orthogonal calibration can provide a transfer matrix for every patient based on the patient's natural postures instead of "standard" postures.

Customization of the posture detection system to a particular patient is possible using calibration processes exemplified by the embodiments described herein. For example, if the patient tends to be humpbacked when standing, calibration with an upright standing posture is difficult to achieve because when the patient is standing naturally, he/she will tilt slightly forward due to the hump. The calibration system of the present invention can be customized to the particular posture of a patient, reducing the requirement that the patient perform unnatural postures for calibration.

Using methods of the present invention, the transfer matrix can be calibrated by asking the patient to stand naturally. For example, if the patient is humpbacked, the patient stands with his/her back humped. The U,V,W, signals for that posture are recorded and the X,Y,Z signals are set to $[a_x \; a_y \; a_z]^T = [0 \; 0 \; -g]^T$, instead of being adjusted for the hump angle. Thus, whenever the patient is performing humpbacked standing, the system recognizes this posture as the standard standing posture for the patient.

An example, where non-orthogonal calibration may be advantageous is when the patient's natural upright posture is stooped, e.g., by about 10 degrees forward. If the gravitational acceleration signals are measured when the subject is standing with a known tilt angle of 10 degrees forward, the X,Y,Z signals at this time are:

$$[a_x, a_y, a_z]^T = [g \sin(10°) \; 0 \; g \cos(10°)]^T, \quad \text{Equation 17}$$

and with measured signals of $[a_u \; a_v \; a_w]^T$, the transfer matrix can be achieved by the same process described above using mutually orthogonal calibration postures. Postures subsequently measured by a system calibrated in this fashion would accurately represent the patient's upright posture as zero degrees.

Posture detection in accordance with the embodiments of the invention involves determining patient postures using a transfer matrix providing enhanced mathematical precision, thus improving the repeatability of the calibration. The process is based on the repeatability of the postures performed during calibration. How well a posture can be determined after calibration is complete depends on whether the subject assumes a posture sufficiently similar to the corresponding posture performed during the calibration process. If a set of measured values, $[a_u \; a_v \; a_w]^T$, are very similar to the U,V,W measured signals recorded for the standing posture during calibration, a set of X,Y,Z signals very close to $[a_x \; a_y \; a_z]^T = [0 \; 0 \; -g]^T$ (Equation 15) can be achieved. Thus, calibration using postures that are repeatable by the patient yields greater accuracy in determining the patient's natural postures.

In accordance with an embodiment of the invention, fine adjustment of the orientation of and implanted device may be achieved based on the calibration processes described herein. For example, three linearly independent postures close to the standing posture can be chosen as the three postures used in the calibration process. Measurements taken while the patient performs the three chosen postures are mapped to the body coordinates X,Y,Z according to the orthogonal equations $[a_x \; a_y \; a_z]^T = [-g \; 0 \; 0]^T$ (Equation 11), $[a_x \; a_y \; a_z]^T = [0 \; -g \; 0]^T$ (Equation 13), and $[a_x \; a_y \; a_z]^T = [0 \; 0 \; -g]^T$ (Equation 15) using the transfer matrix of Equations 9, 12, 14, and 16. By this calibration, the three linearly independent gravitational vectors for the three chosen postures determine a small spherical triangle surface. After applying the inverse transfer matrix, this small surface will be mapped to a ⅛ spherical surface. Thus, every small tilting angle around the standing posture will be magnified in the X,Y,Z coordinates. Calibration in accordance with this process makes the posture detection for the standing/sifting upright posture very sensitive. A similar process may alternatively be applied to enhance posture detection resolution for other orientations.

Embodiments of the invention involve approaches for determining the posture of the patient, such as determining the tilt angle of the patient. The systems for detecting patient posture may be calibrated using the calibration processes described above, or may be calibrated using other processes.

Conventional implantable posture detection systems produce posture results that are demonstrated only qualitatively. These systems display only posture status, such as whether the patient is standing or lying down. Approaches of the present invention are capable of reporting posture quantitatively, e.g., in terms of tilt angle, in contrast to the qualitative methods previously described.

Figure 4:
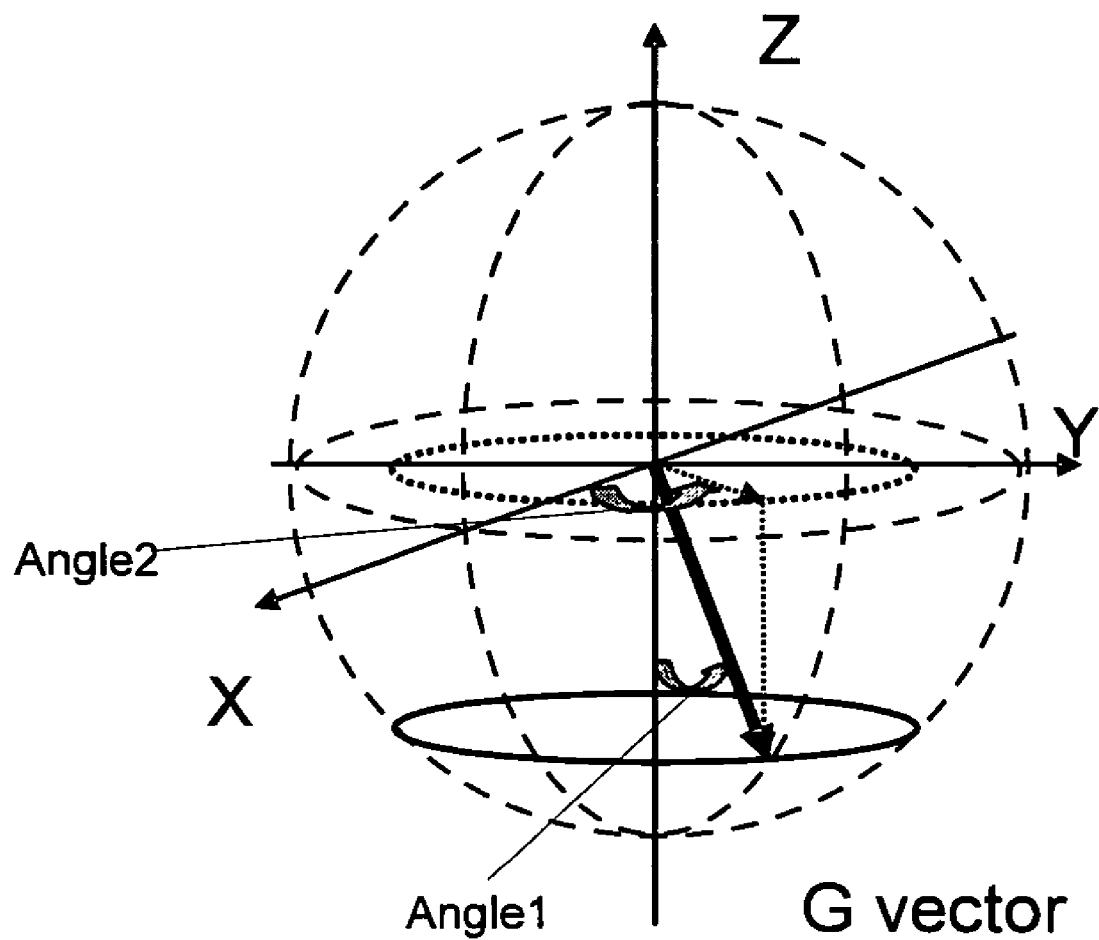
FIG. 4 illustrates a spherical gravitational G vector surface used for posture detection in accordance with embodiments of the present invention.

Posture sensing methods in accordance with embodiments of the present invention are based on the use of a spherical gravitational G vector surface. As illustrated in FIG. 4, when the body coordinate system is chosen as the reference coordinate system, the gravitational acceleration vector G for any possible posture may be mapped to a certain point on a spherical surface, with radius the magnitude of the G vector. The orientation of the G vector can be determined by two rotational angles, designated Angle1 and Angle2. In the example depicted in FIG. 4, Angle1 is defined as the polar angle between the vector G and the negative Z direction. Angle2 is defined as the azimuthal angle between the projected vector G on the X/Y plane and the positive X axis.

Mathematically, Angle1 may be calculated as follows:

$$\text{Angle1} = a\cos\left(\frac{-z}{\sqrt{x^2+y^2+z^2}}\right).\qquad\text{Equation 18}$$

Angle2 may be calculated, $$\text{Angle2} = a\cos\left(\frac{x}{\sqrt{x^2+y^2}}\right), \text{ if } y > 0,\qquad\text{Equation 19}$$

and $$\text{Angle2} = -a\cos\left(\frac{x}{\sqrt{x^2+y^2}}\right), \text{ if } y < 0.\qquad\text{Equation 20}$$

Angle1 and Angle2 provide detailed information about the patient postures and may be defined as the quantitative outputs for posture classification. For example, based on Angle 1 and Angle 2, the posture sensing device may report four or more intermediate tilting postures such as Tilting forward, Tilting Backward, Tilting Right and Tilting Left.

Figure 5B:
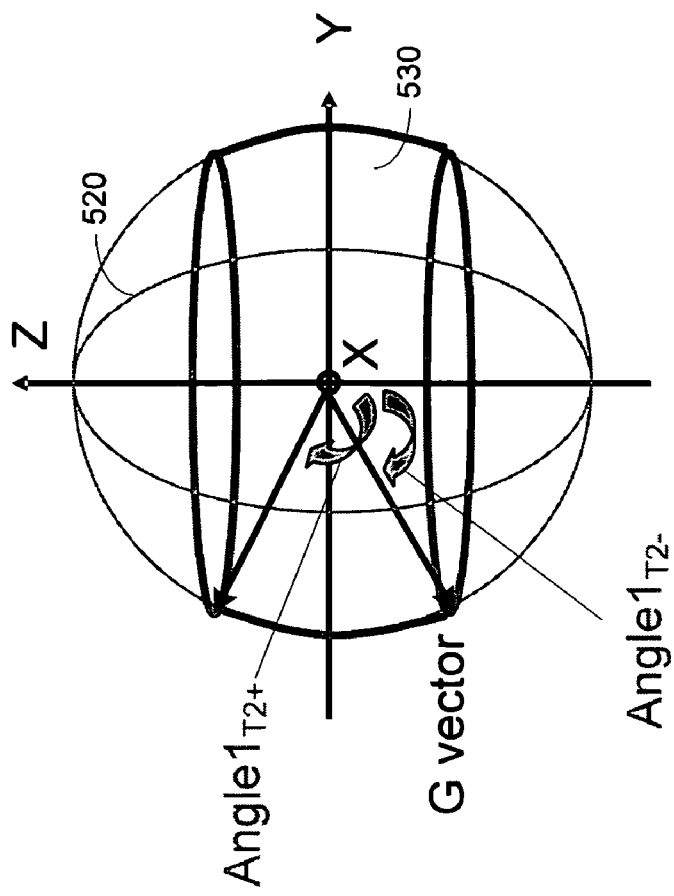
FIG. 5B illustrates a second threshold region defined by a second threshold angle, $Angle1_{T2}$, in accordance with embodiments of the invention.
Figure 5A:
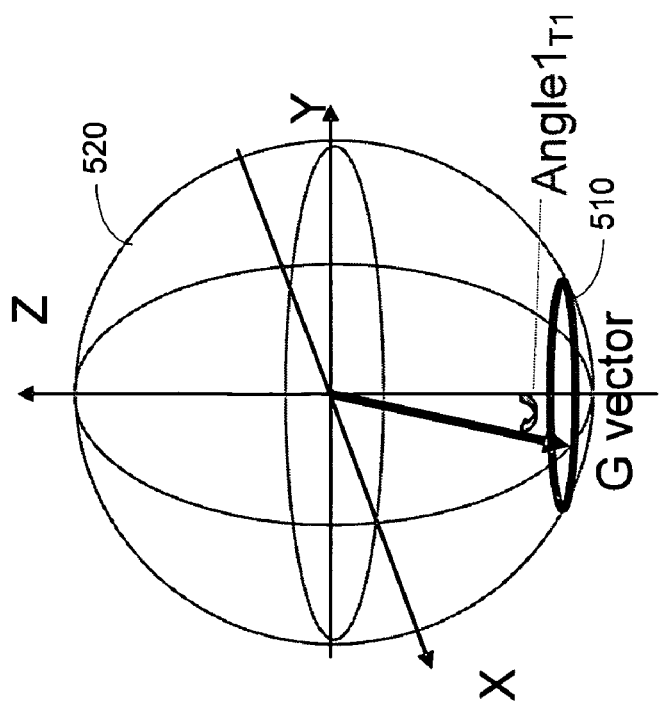
FIG. 5A illustrates a first threshold region defined by a first threshold angle, $Angle1_{T1}$, in accordance with embodiments of the invention.

Posture determination may be achieved by setting up threshold regions on the G vector spherical surface corresponding to various postures. For example, threshold regions may be defined as illustrated in FIGS. 5A and 5B. FIG. 5A illustrates a first threshold region 510 which corresponds to the intersection of a cone surface defined by a threshold angle, Angle1$_{T1}$ and the total spherical G vector surface 520. If the G vector is pointing in threshold region 510, then the patient's posture is classified as standing/sitting upright.

FIG. 5B provides a view, looking through the X axis, of the G vector surface 520. A second threshold region 530 is defined as a ring section along the equator of the G vector surface 510 defined by the threshold angles, Angle1$_{T2-}$ and Angle1$_{T2+}$, between the G vector and the −Z axis. If the G vector is pointing in threshold region 530, then the posture is classified as lying down.

Figure 5C:
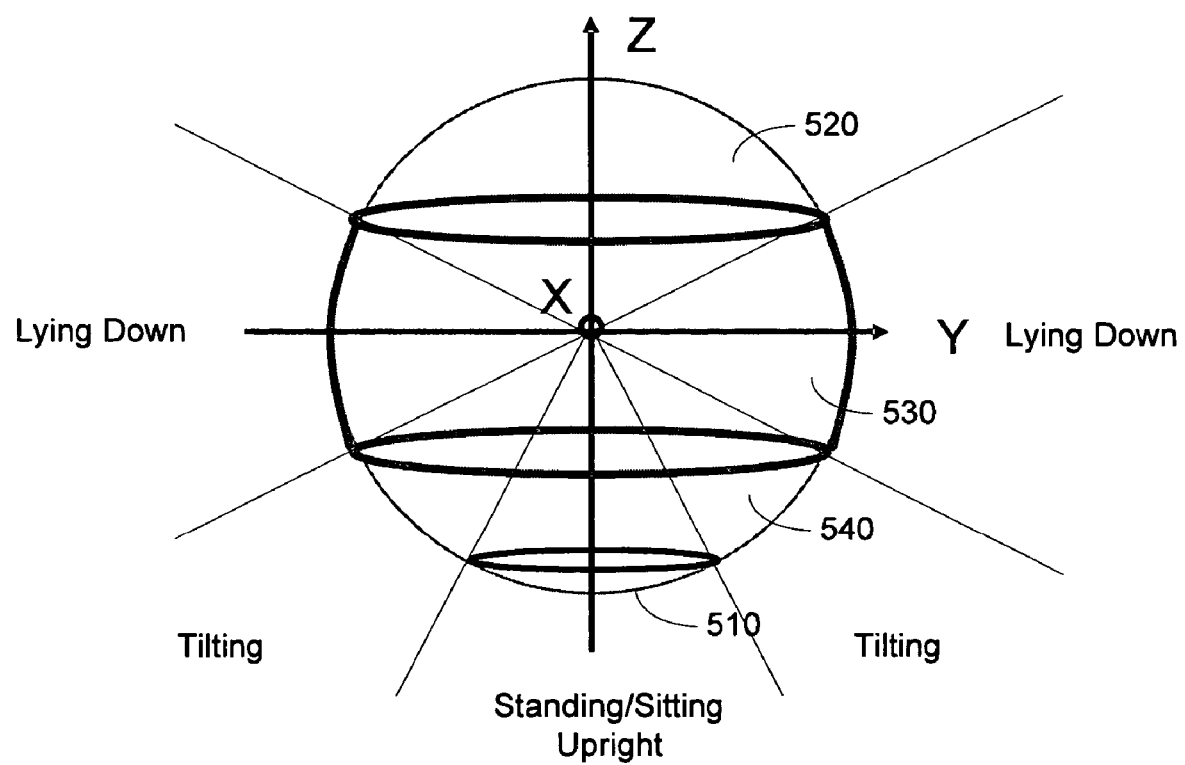
FIG. 5C illustrates possible patient postures including a standing/sitting upright posture, a lying down posture, and a tilting posture.

Looking through the X axis, FIG. 5C illustrates possible patient postures including a standing/sitting upright posture, a lying down posture, and a tilting posture. If the G vector points in the first threshold region 510, then the patient is classified as having a standing/sitting upright posture. If the G vector points in the second threshold region 530, then the patient is classified as having a lying down posture. FIG. 5C shows an intermediate tilting section 540 between the first threshold region 510 and the second threshold region 530. If the G vector points in the intermediate section 540, then the patient classified as having a tilting posture.

Figure 5D:
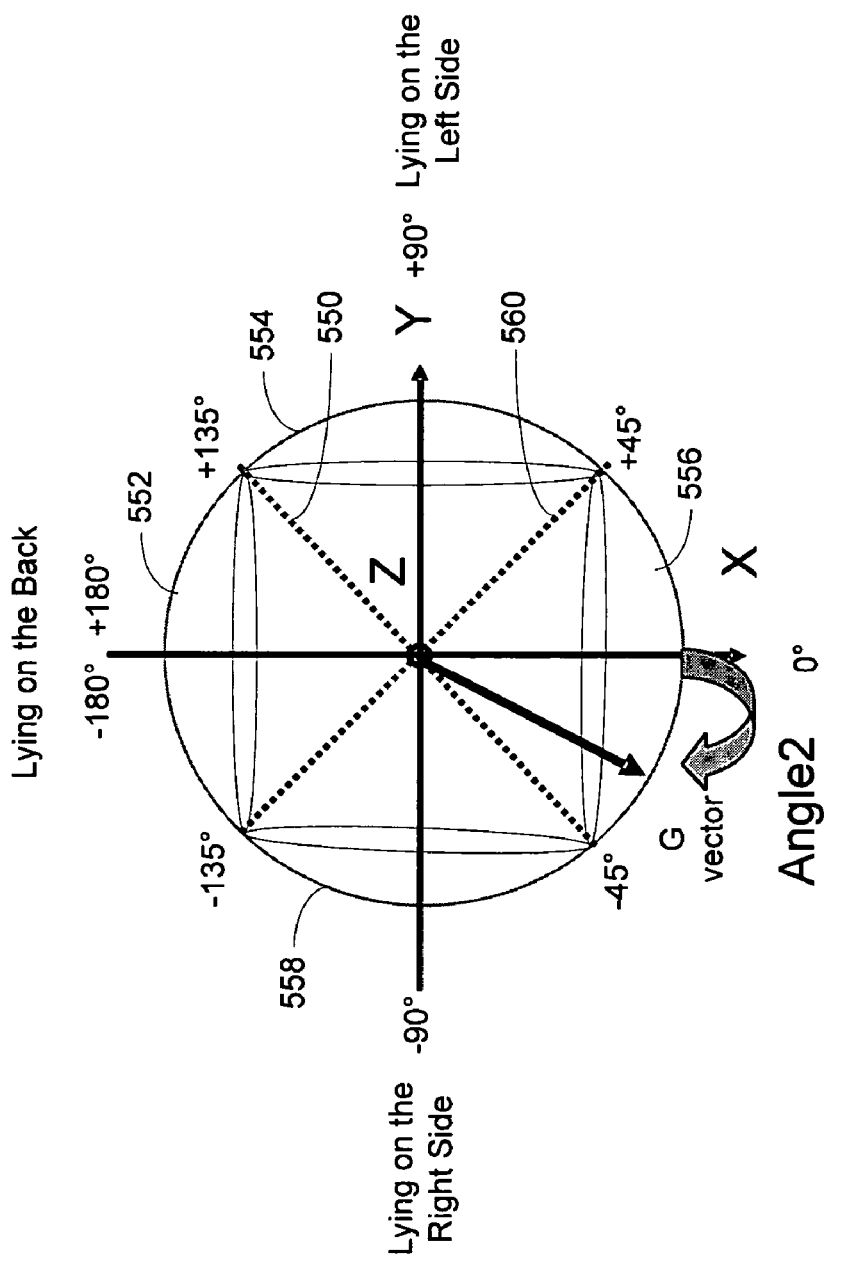
FIG. 5D illustrates four posture detection regions in accordance with embodiments of the invention.

FIG. 5D shows a view of the G vector surface looking through the Z axis. As depicted in FIG. 5D, the Lying down region 530 (FIG. 5C) and the Tilting region 540 (FIG. 5C) can be subdivided into four parts 552, 554, 556, 558, for example, by 45° lines 550 and 560. Angles other than 450 may alternatively be used to subdivide the tilting region. When the G vector points in section 556 along the positive X direction, the patient is lying on his/her stomach or tilting forward. When the G vector points in section 552 along the negative X direction, the patient is lying on his/her back or tilting backward. When the G vector points in section 554 along the positive Y direction the patient is lying on his/her left side or tilting left. When the G vector points in section 558 along the negative Y direction, the patient is lying on his/her right side or tilting right.

FIG. 6 is a flowchart of a posture detection algorithm in accordance with embodiments of the invention. The posture of the patient is determined using threshold angles, Angle1$_{T1}$, Angle1$_{T2-}$ and Angle1$_{T2+}$, and the 45' thresholds on Angle2 as previously described. The angle between the G vector and the Z axis, Angle1, is calculated and is used to initially determine the posture as one of the following postures: upside down, standing/sitting upright, lying down, or tilting. If Angle1 is greater than Angle1$_{T2+}$, then the patient is upside down. If Angle1 is less than Angle1$_{T1}$ then the patient is standing or sitting upright. If Angle1 is greater than Angle1$_{T2-}$ and is less than Angle1$_{T2+}$, then the patient is lying down. If Angle1 is >Angle1$_{T1}$ and Angle1<Angle1$_{T2-}$, then the patient is tilting.

If the patient is lying down, the system uses Angle2 to determine if the patient is lying on the stomach, back, left side or right side. If Angle2 is between −45° and 45° then the patient is lying on the stomach. If Angle2 is between 45° and 135° then the patient is lying on the left side. If Angle2 is between −135° and −45° then the patient is lying on the right side. If Angle2 is between 135° and 180° or between −180° and −135° then the patient is lying on the back.

Similarly, if the patient is tilting down, the system uses Angle2 to determine if the patient is tilting forward, backward, to the left side or to the right side. If Angle2 is between −45° and 45° then the patient is tilting forward. If Angle2 is between 45° and 135° then the patient is tilting to the left side. If Angle2 is between −135° and −45° then the patient is tilting to the right side. If Angle2 is between 135° and 180° or between −180° and −135° then the patient is tilting backward.

Using the calibration process described herein, Angle1 and Angle2 may be calculated with a resolution finer than about 5°. The enhanced resolution of the posture sensing system may be exploited to study the progression or regression of various medical conditions that are associated with certain patient postures. In one implementation, the patient's tilt angle during sleep may be determined and tracked over a period of time. The posture of the patient may be correlated to certain medical conditions, such as disordered breathing, pulmonary disease, and/or congestive heart failure.

In one example, an implantable medical device may determine the patient position and also may detect respiration disturbances such as sleep apnea. A correlation between an increase or decrease in sleep apnea episodes and a particular tilt angle may be determined. The correlation may be made by the implantable device, or information related to tilt angle and respiration disturbance may be telemetered to a remote device, such as an advanced patient management (APM) system for further analysis. Various embodiments described herein may be used in connection with advanced patient management. Methods, structures, and/or techniques described herein relating to advanced patient management, such as those involving remote patient/device monitoring, diagnosis, therapy, or other advanced patient management related methodologies, may incorporate features of one or more of the following references: U.S. Pat. Nos. 6,221,011; 6,277,072; 6,280,380; 6,358,203; 6,368,284; and 6,440,066 each hereby incorporated herein by reference.

In another example, tracking tilt angle over a period of time may be used to track the progression or regression of heart failure. Tracking tilt angle may also be used to assess the effectiveness of heart failure treatments including cardiac resynchronization therapy such as biventricular pacing. Heart failure patients typically have difficulty breathing when they are in a recumbent position. These patients typically sleep using several pillows or other support so that their torso is tilted upward from the prone position. Tracking the tilt angle during sleep over a period of time provides insight into the severity and progression of heart failure decompensation. For example, if the tilt angle during sleep increases over time, then the patient's heart failure symptoms may be increasing in severity. Conversely, if the tilt angle during sleep decreases over time, heart failure decompensation may be improving. If the patient is receiving treatment for heart failure, such as CRT, then the improvement in heart failure decompensation may be attributed to the therapy.

Embodiments of the posture calibration and posture sensing system illustrated herein are generally described as being implemented in a patient internal device that includes cardiac rhythm management (CRM) circuitry. The CRM circuitry may operate to detect and deliver multi-level therapy for treatment of cardiac arrhythmias. Various types of single and multiple chamber CRM devices may be used to implement a number of electrical stimulation therapies as are known in the art, including pacing therapy, cardioversion and/or defibrillation. The CRM circuitry may operate to provide cardiac resynchronization therapy and may be capable of delivering biventricular pacing therapy for the treatment of congestive heart failure.

It is understood that configurations, features, and combination of features described in the present disclosure can be implemented in a wide range of implantable or external medical devices, and that such embodiments and features are not limited to the particular devices described herein. The systems and methods described herein may be implemented in a wide variety of implantable or external diagnostic and/or therapeutic devices such as defibrillators, cardioverters, pacemakers, cardiac monitors, and resynchronizers, for example.

Figure 7:
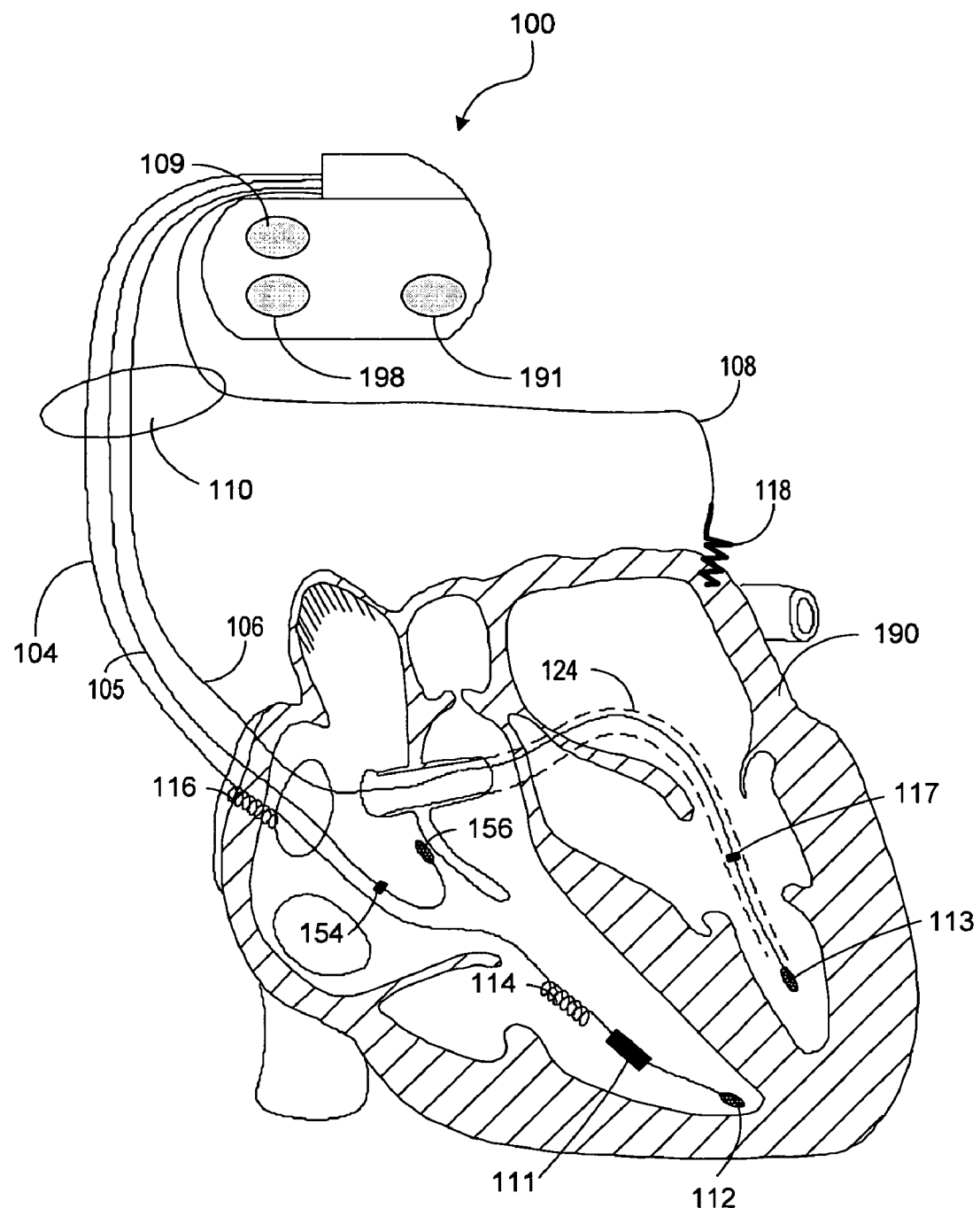
FIG. 7 is a partial view of an implantable device that may include circuitry for implementing portions of a posture detection system in accordance with embodiments of the invention.

Referring now to FIG. 7 of the drawings, there is shown one embodiment of an implantable device that may be used to implement the calibration and posture sensing methods of the present invention. The implantable device 100 illustrated in FIG. 6 includes a cardiac pulse generator (PG) electrically and physically coupled to a lead system 110. The posture calibration 109 and/or posture sensing 198 systems of the present invention along with a multi-axis accelerometer 191 may be disposed within the can of the implantable device 100.

The housing and/or header of the implantable device 100 may incorporate one or more electrodes used to provide electrical stimulation energy to the heart and to sense cardiac electrical activity. All or a portion of the implantable device housing may be configured as a can electrode. The implantable device 100 may include an indifferent electrode positioned, for example, on the header or the housing of the implantable device 100.

The lead system 110 is used to detect electrical signals produced by the heart 190 and to provide electrical energy to the heart 190 under certain predetermined conditions to treat cardiac arrhythmias. The lead system 110 may include one or more electrodes used for pacing, sensing, and/or cardioversion/defibrillation. In the embodiment shown in FIG. 7, the lead system 110 includes an intracardiac right ventricular (RV) lead system 104, an intracardiac right atrial (RA) lead system 105, an intracardiac left ventricular (LV) lead system 106, and an extracardiac left atrial (LA) lead system 108. The lead system 110 of FIG. 7 illustrates one embodiment that may be used in connection with the multi level tachyarrhythmia therapy methodologies described herein. Other leads and/or electrodes may additionally or alternatively be used.

The lead system 110 may include intracardiac leads 104, 105, 106 implanted in a human body with portions of the intracardiac leads 104, 105, 106 inserted into a heart 190. The intracardiac leads 104, 105, 106 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 7, the lead system 110 may include one or more extracardiac leads 108 having electrodes, e.g., epicardial electrodes, positioned at locations outside the heart for sensing and/or pacing one or more heart chambers.

The right ventricular lead system 104 illustrated in FIG. 6 includes an SVC-coil 116, an RV-coil 114, an RV-ring electrode 111, and an RV-tip electrode 112. The right ventricular lead system 104 extends through the right atrium and into the right ventricle. In particular, the RV-tip electrode 112, RV-ring electrode 111, and RV-coil electrode 114 are positioned at appropriate locations within the right ventricle for sensing and delivering electrical stimulation pulses to the heart. The SVC-coil 116 is positioned at an appropriate location within the right atrium chamber of the heart 190 or a major vein leading to the right atrial chamber of the heart 190.

In one configuration, the RV-tip electrode 112 referenced to the can electrode may be used to implement unipolar pacing and/or sensing in the right ventricle. Bipolar pacing and/or sensing in the right ventricle may be implemented using the RV-tip 112 and RV-ring 111 electrodes. The RV-ring 111 electrode may optionally be omitted, and bipolar pacing and/or sensing may be accomplished using the RV-tip electrode 112 and the RV-coil 114, for example. Sensing in the RV may involve the tip-to-ring vector and the RV-coil to SVC-coil or the RV-coil to SVC coil electrically tied to the can vector. The right ventricular lead system 104 may be configured as an integrated bipolar pace/shock lead. The RV-coil 114 and the SVC-coil 116 are defibrillation electrodes.

The left ventricular lead 106 includes an LV distal electrode 113 and an LV proximal electrode 117 located at appropriate locations in or about the left ventricle for pacing and/or sensing the left ventricle. The left ventricular lead 106 may be guided into the right atrium of the heart via the superior vena cava. From the right atrium, the left ventricular lead 106 may be deployed into the coronary sinus ostium, the opening of the coronary sinus. The lead 106 may be guided through the coronary sinus to a coronary vein 124 of the left ventricle. This vein is used as an access pathway for leads to reach the surfaces of the left ventricle that are not directly accessible from the right side of the heart. Lead placement for the left ventricular lead 106 may be achieved via subclavian vein access and a preformed guiding catheter for insertion of the LV electrodes 113, 117 adjacent to the left ventricle.

Unipolar pacing and/or sensing in the left ventricle may be implemented, for example, using the LV distal electrode 113 referenced to the can electrode. The LV distal electrode 113 and the LV proximal electrode 117 may be used together as bipolar sense and/or pace electrodes for the left ventricle. The left ventricular lead 106 and the right ventricular lead 104, in conjunction with the PG 100, may be used to provide cardiac resynchronization therapy such that the ventricles of the heart are paced substantially simultaneously, or in phased sequence, to provide enhanced cardiac pumping efficiency for patients suffering from chronic heart failure.

The right atrial lead 105 includes a RA-tip electrode 156 and an RA-ring electrode 154 positioned at appropriate locations in the right atrium for sensing and pacing the right atrium. In one configuration, the RA-tip 156 referenced to the can electrode, for example, may be used to provide unipolar pacing and/or sensing in the right atrium. In another configuration, the RA-tip electrode 156 and the RA-ring electrode 154 may be used to effect bipolar pacing and/or sensing.

FIG. 7 illustrates one embodiment of a left atrial lead system 108. In this example, the left atrial lead 108 is implemented as an extracardiac lead with an LA distal electrode 118 positioned at an appropriate location outside the heart 190 for sensing and pacing the left atrium. Unipolar pacing and/or sensing of the left atrium may be accomplished, for example, using the LA distal electrode 118 to the can vector. The left atrial lead 108 may be provided with additional electrodes used to implement bipolar pacing and/or sensing of the left atrium.

Figure 8:
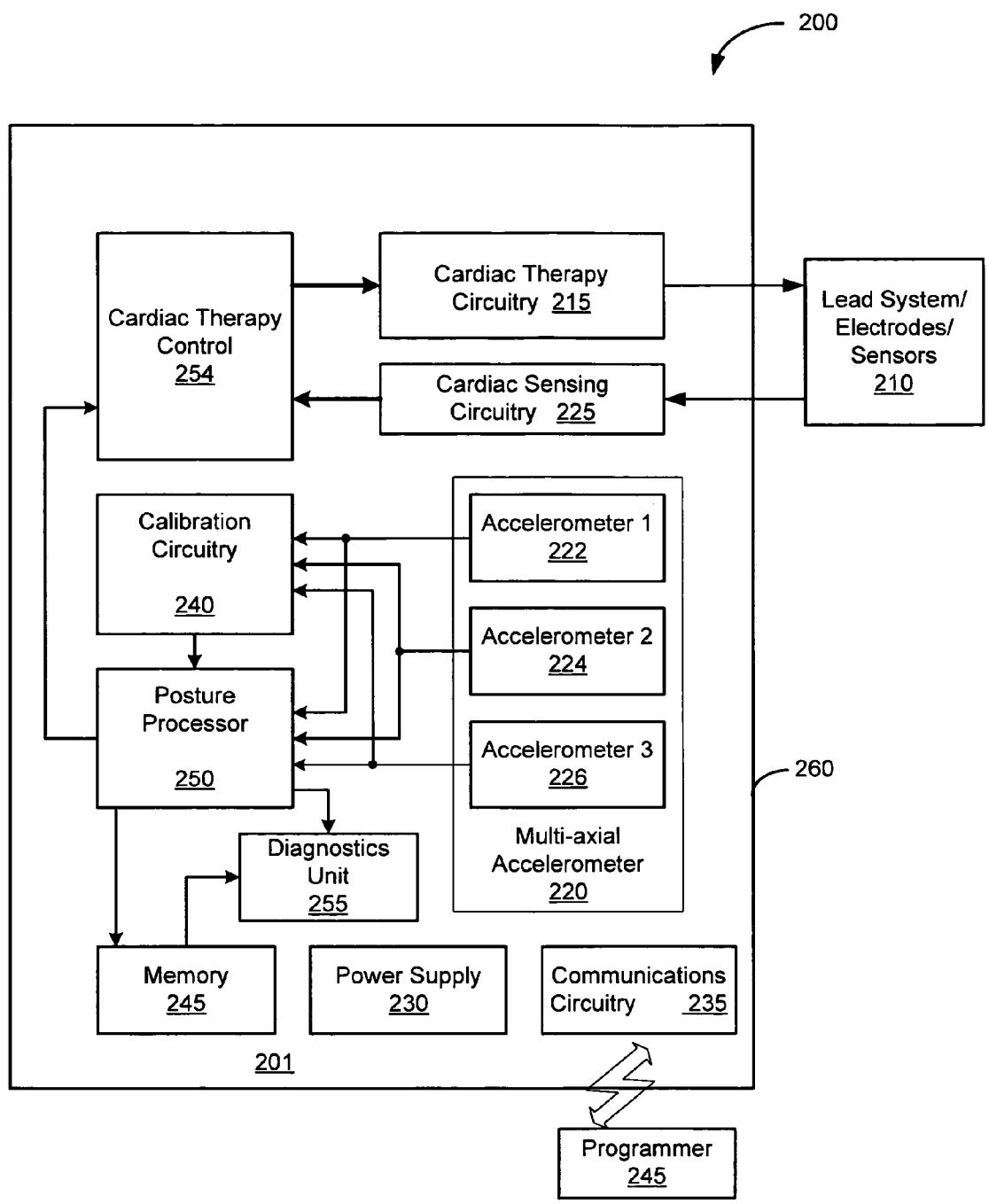
FIG. 8 is a block diagram of an implantable device illustrating possible components of a posture detection system in accordance with embodiments of the invention.

Referring now to FIG. 8, there is shown a block diagram of an embodiment of an implantable device 200 suitable for implementing posture calibration and/or posture sensing methodologies of the present invention. FIG. 8 shows the implantable device 200 divided into functional blocks. There exist many possible configurations in which these functional blocks can be arranged. The example depicted in FIG. 8 is one possible functional arrangement. The implantable device 200 depicted in FIG. 8 includes CRM circuitry including cardiac sensing circuitry for receiving cardiac signals from a heart and delivering electrical energy in the form of pace pulses or cardioversion/defibrillation pulses to the heart.

The housing of the implantable device encloses a multi-axis orientation sensor 220, comprising, for example, three DC uniaxial accelerometers 222, 224, 226. The sensitive axes of the three uniaxial accelerometers are typically positioned to be mutually orthogonal as described above. When the device 200 is implanted within the patient's body, the accelerometers 222, 224, 226 produce signals corresponding to the orientation of the device with respect to the earth's gravitational force. The outputs of the accelerometers 222, 224, 226 may be coupled to calibration circuitry 240 used to perform posture calibration according to the methods of the present invention. The outputs of the accelerometers 222, 224, 226 and the calibration circuitry 240 may also be coupled to a posture processor 250. The posture processor 250 may be used to determine patient position including tilt angle in accordance with the posture determination methodologies of the present invention described herein.

In the embodiment illustrated in FIG. 8, the posture detector, including the multi-axis orientation sensor 220, calibration circuitry 240 and posture processor 250 are disposed within the housing of the implantable device 260 along with CRM circuitry. A cardiac lead system 210 may be implanted so that cardiac electrodes are electrically coupled to the heart tissue as described above in connection with FIG. 7. The cardiac electrodes of the lead system 210 along with sensing circuitry 225 disposed within the implantable device housing are used to sense cardiac signals associated with electrical activity of the heart.

The cardiac electrodes and lead system 210 may also be used to deliver electrical stimulation pulses or shocks generated by the cardiac therapy circuitry 215 to the heart for treating various cardiac arrhythmias. The CRM circuitry, including the therapy control circuitry 254, cardiac sensing circuitry 225, cardiac therapy circuitry 215, and cardiac electrodes/lead system 210, may detect cardiac signals and deliver therapeutic electrical stimulation to any of the left and right ventricles and left and right atria, for example. In some implementations, the therapy control circuitry may use posture information to modify therapy delivered to the patient. For example, if the posture information indicates the patient is lying down and sleeping, the rate of pacing pulses may be delivered as a sleep pacing rate that is different from the pacing rate delivered while the patient is upright and awake.

Power to the implantable device 260 is supplied by an electrochemical battery 230 that is housed within the implantable device 260. The implantable device 260 may also include a memory 245. The memory 245 may be used to store posture information for tracking changes in patient posture over time. In some implementations, the implantable device 260 may incorporate a diagnostics processor 255 that utilizes posture information stored in memory 240, possibly along with other information, to detect the presence or track the progression of various medical disorders. In another implementation, the diagnostics processor is incorporated in a remote patient external device. The posture information, along with other parameters and data stored in the memory 240, may be transmitted via telemetry to an external programmer unit 245 or other patient-external device, as desired.

Communications circuitry 235 allows the implantable device 260 to communicate with an external programmer unit 245 and/or other patient-external system(s). In one embodiment, the communications circuitry 235 and the programmer unit 245 use a wire loop antenna and a radio frequency telemetric link to receive and transmit signals and data between the programmer 245 and communications circuitry 235. In this manner, programming commands and/or other information may be transferred to the implantable device 260 from the programmer 245 during and after implant.

A number of the examples presented herein involve block diagrams illustrating functional blocks used for in accordance with embodiments of the present invention. It will be understood by those skilled in the art that there exist many possible configurations in which these functional blocks can be arranged and implemented.

The examples depicted herein provide examples of possible functional arrangements used to implement the approaches of the invention. The components and functionality depicted as separate or discrete blocks/elements in the figures in general can be implemented in combination with other components and functionality. The depiction of such components and functionality in individual or integral form is for purposes of clarity of explanation, and not of limitation. It is also understood that the components and functionality depicted in the Figures and described herein can be implemented in hardware, software, or a combination of hardware and software.

Methods, devices, and systems in accordance with the present invention may incorporate one or more of the features, structures, methods, or combinations thereof described herein. For example, a medical system may be implemented to include one or more of the features and/or processes described herein. It is intended that such a method, device, or system need not include all of the features and functions described herein, but may be implemented to include one or more selected features and functions that provide unique structures and/or functionality.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method for operating a medical device to detect posture, comprising:
measuring outputs of one or more sensors disposed in relation to a patient's body while the patient assumes a plurality of body postures, the one or more sensors responsive to a gravitational field;
forming a transfer matrix using a processor, the transfer matrix having coefficients, each coefficient being proportional to one of the measured outputs
to define a relationship between a coordinate system of the one or more sensors and a coordinate system of the patient's body different from the coordinate system of the one or more sensors; and
determining, using the processor, a posture of the patient's body using the body coordinate system as a reference coordinate system;
wherein at least one of the measuring, forming, and determining is carried out by the medical device.

2. The method of claim 1, wherein the coefficients comprise the measured outputs divided by a magnitude of the gravitational field.

3. The method of claim 1, wherein measuring the outputs of the one or more sensors comprises measuring the outputs of one or more accelerometers.

4. The method of claim 3, wherein sensitive axes of at least two accelerometers are oriented substantially orthogonally.

5. The method of claim 1, wherein measuring the outputs of the one or more sensors comprises measuring the outputs of the one or more sensors while the patient assumes two or more substantially mutually orthogonal body postures.

6. The method of claim 1, wherein measuring the outputs of the one or more sensors while the patient assumes the plurality of body postures comprises:
measuring the outputs of the one or more sensors while the patient is upright or upside down;
measuring the outputs of the one or more sensors while the patient is lying on a right side or lying on a left side; and
measuring the outputs of the one or more sensors while the patient is prone or supine.

7. The method of claim 1, wherein at least one of measuring the outputs of the one or more sensors, forming the transfer matrix, and determining the posture of the patient's body is performed at least in part implantably.

8. The method of claim 1, wherein determining the posture of the patient's body comprises determining tilt of the patient's body.

9. The method of claim 1, wherein determining the posture of the patient's body comprises determining a tilt angle of the patient's body.

10. The method of claim 9, wherein determining the tilt angle comprises determining the tilt angle to within about five degrees with respect to a plane.

11. The method of claim 1, wherein determining the posture of the patient's body comprises:
determining first and second rotational angles associated with posture;
comparing the first and the second rotational angles to threshold values; and
determining the posture based on the comparisons.

12. A posture detector, comprising:
one or more sensors responsive to a gravitational field, each sensor disposed in relation to a patient's body and configured to output a signal based on an orientation of the patient;
calibration circuitry coupled to the one or more sensors and configured to form a transfer matrix having coefficients, each coefficient being proportional to one of the sensor outputs, the transfer matrix defining a relationship between a coordinate system of the one or more sensors and a coordinate system of the patient's body different from the coordinate system of the one or more sensors; and
a posture processor coupled to the one or more sensors and the calibration circuitry and configured to determine a posture of the patient's body using the body coordinate system as a reference coordinate system.

13. The posture detector of claim 12, wherein coefficients of the transfer matrix comprise the sensor outputs divided by a magnitude of the gravitational field.

14. The posture detector of claim 12, wherein sensitive axes of the one or more sensors are oriented substantially orthogonally.

15. The posture detector of claim 12, wherein at least one of the one or more sensors, the calibration circuitry, and the posture processor comprise an implantable component.

16. The posture detector of claim 12, wherein the one or more sensors comprise one or more accelerometers.

17. The posture detector of claim 12, wherein the posture processor is configured to determine a tilt of the patient's body.

18. The posture detector of claim 12, wherein the posture processor is configured to determine a tilt angle of the patient's body.

19. The posture detector of claim 12, further comprising a diagnostics processor configured to determine a presence cardiac decompensation based on the tilt angle.

20. The posture detector of claim 12, wherein the diagnostics processor is configured to track progression of disease based on changes in the tilt angle.

21. A posture sensing system, comprising:
means for measuring outputs of one or more sensors responsive to a gravitational field disposed in relation to a patient's body while the patient assumes a plurality of body postures;
means for forming a transfer matrix having coefficients, each coefficient being proportional to one of the measured outputs, the transfer matrix defining a relationship between a coordinate system of the one or more sensors and a coordinate system of the patient's body different from the coordinate system of the one or more sensors; and
means for determining a posture of the patient's body using the body coordinate system as a reference coordinate system.

22. The system of claim 21, further comprising means for determining a tilt angle of the patient's body.

23. A method for operating a medical device to detect posture, comprising:
measuring outputs from a plurality of accelerometers disposed in the medical device with relation to a patient's body, each accelerometer providing its output based on the accelerometer's orientation with respect to gravity;
determining, using a processor, first and second rotational angles associated with posture using the measured accelerometer outputs;
comparing, using the processor, the first and the second rotational angles to threshold regions on a spherical surface; and
determining, using the processor, the posture based on the comparisons;
wherein at least one of the determining first and second rotational angles, comparing, and determining the posture is carried out by the medical device.

24. The method of claim 23, wherein:
- determining the first rotational angle comprises determining a polar angle with respect to a first axis of a body coordinate system; and
- determining the second rotational angle comprises determining an azimuthal angle within a plane of a second and third axis of the body coordinate system.

25. The method of claim 24, wherein the first axis of the body coordinate system is oriented substantially along the inferior-superior axis of the patient's body.

26. The method of claim 24, wherein the first, second and third axes are substantially mutually orthogonal, and one of the second or third axes is oriented substantially along the anterior-posterior axis of the patient's body.

27. The method of claim 23, wherein determining the first and the second rotational angles comprises:
- defining a vector associated with the posture;
- determining the posture based on an orientation of the vector with respect to a body coordinate system.

28. The method of claim 23, wherein determining the posture of the patient's body comprises determining tilt of the patient's body.

29. The method of claim 23, wherein determining the posture of the patient's body comprises determining a tilt angle of the patient's body.

30. A posture detector, comprising:
- one or more sensors responsive to a gravitational field disposed in relation to a patient's body, each sensor configured to output a signal based on an orientation of the patient; and
- a posture processor coupled to the one or more sensors and configured to determine first and second rotational angles associated with the posture from the sensor outputs, to compare the first and second rotational angles to threshold regions on a spherical surface, and to determine the posture based on the comparisons.

31. The posture detector of claim 30, wherein the one or more sensors comprise one or more accelerometers.

32. The posture detector of claim 30, wherein:
- the first rotational angle comprises a polar angle with respect to a first axis of a body coordinate system; and
- the second rotational angle comprises an azimuthal angle within a plane of the second and third axes of the body coordinate system.

33. The posture detector of claim 32, wherein the first axis of the body coordinate system is oriented substantially along the inferior-superior axis of the patient's body.

34. The posture detector of claim 32, wherein the first, second and third axes are substantially mutually orthogonal, and one of the second or third axes is oriented substantially along the anterior-posterior axis of the patient's body.

35. The posture detector of claim 30, wherein the posture processor is configured to define a vector associated with the posture and to determine the posture based on an orientation of the vector with respect to a body coordinate system.

36. The posture detector of claim 30, wherein the posture processor is configured to determine a tilt angle of the patient's body.

37. A posture sensing system, comprising:
- means for measuring outputs from a plurality of accelerometers disposed in a medical device with relation to a patient's body, each accelerometer providing its output based on the accelerometer's orientation with respect to gravity;
- means for determining first and second rotational angles associated with posture using the measured accelerometer outputs;
- means for comparing the first and the second rotational angles to threshold regions on a spherical surface; and
- means for determining the posture based on the comparisons.

38. The system of claim 37, further comprising:
- means for determining a polar angle with respect to a first axis of a body coordinate system; and
- means for determining an azimuthal angle within a plane of a second and third axis of the body coordinate system.

39. The system of claim 38, wherein the first axis of the body coordinate system is oriented substantially along the inferior-superior axis of the patient's body.

40. The system of claim 38, wherein the first, second, and third axes are substantially mutually orthogonal, and one of the second or third axes is oriented substantially along the anterior-posterior axis of the patient's body.

41. The system of claim 37, further comprising:
- means for defining a vector associated with the posture; and
- means for determining the posture based on an orientation of the vector with respect to a body coordinate system.

42. The system of claim 37, further comprising means for determining a tilt angle of the patient's body.

* * * * *